(12) United States Patent
Ishizaki et al.

(10) Patent No.: US 10,299,659 B2
(45) Date of Patent: May 28, 2019

(54) INSERTION INSTRUMENT AND INSERTION DEVICE

(71) Applicant: OLYMPUS CORPORATION, Tokyo (JP)

(72) Inventors: Ryosuke Ishizaki, Fuchu (JP); Takehiro Nishiie, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/620,917

(22) Filed: Jun. 13, 2017

(65) Prior Publication Data

US 2017/0279237 A1 Sep. 28, 2017

Related U.S. Application Data

(63) Continuation of application No. PCT/JP2016/059723, filed on Mar. 25, 2016.

(30) Foreign Application Priority Data

Jun. 5, 2015 (JP) .................................. 2015-114889

(51) Int. Cl.
  *A61B 1/00* (2006.01)
  *G02B 23/24* (2006.01)

(52) U.S. Cl.
  CPC ........ *A61B 1/00073* (2013.01); *A61B 1/0016* (2013.01); *A61B 1/00135* (2013.01);
  (Continued)

(58) Field of Classification Search
  CPC ............ A61B 1/00073; A61B 1/00135; A61B 1/00154; A61B 1/00156; A61B 1/0016;
  (Continued)

(56) References Cited

U.S. PATENT DOCUMENTS

| | | | |
|---|---|---|---|
| 2013/0035552 A1* | 2/2013 | Moriyama | ......... A61B 1/00073 600/149 |
| 2014/0330079 A1 | 11/2014 | Ishizaki et al. | |

FOREIGN PATENT DOCUMENTS

| | | |
|---|---|---|
| JP | 2014-073320 A | 4/2014 |
| WO | WO 2007/020687 A1 | 2/2007 |

(Continued)

OTHER PUBLICATIONS

Chinese Office Action dated Mar. 19, 2018 in Chinese Patent Application No. 201680004143.7.

(Continued)

*Primary Examiner* — Aaron B Fairchild
(74) *Attorney, Agent, or Firm* — Scully, Scott, Murphy & Presser, P.C.

(57) ABSTRACT

An insertion device includes an insertion section extending along a longitudinal axis, a rotor provided in the insertion section rotating around the longitudinal axis, and an assistance tool attached to the insertion section in a state to cover the rotor from an outer peripheral side. The assistance tool rotates around the longitudinal axis together with the rotor when press force is applied from a first projection of the rotor to a second projection of the assistance tool by a rotation of the rotor. An angular position of the second projection around the longitudinal axis can be recognized from an outside of the assistance tool.

12 Claims, 9 Drawing Sheets

(52) U.S. Cl.
CPC ...... *G02B 23/2476* (2013.01); *A61B 1/00002* (2013.01); *G02B 23/24* (2013.01)

(58) Field of Classification Search
CPC ............ A61B 1/00131; A61B 1/00133; A61B 1/00137; E03F 9/005; H01R 39/28; H01R 39/64; B08B 9/045; B08B 9/047; F16H 7/02; F16H 57/01
See application file for complete search history.

(56) References Cited

FOREIGN PATENT DOCUMENTS

| WO | WO 2013/038720 A1 | 3/2013 |
| WO | WO 2014/208333 A1 | 12/2014 |
| WO | WO 2015/072233 A1 | 5/2015 |

OTHER PUBLICATIONS

English translation of the Written Opinion of the International Searching Authority from International Application No. PCT/JP2016/059723 dated Aug. 17, 2017.
International Search Report dated Jun. 21, 2016 issued in PCT/JP2016/059723.
Extended Supplementary European Search Report dated Jul. 19, 2018 in European Patent Application No. 16 80 2890.0.
Chinese Office Action dated Jan. 22, 2019 in Chinese Patent Application No. 201680004143.7.

\* cited by examiner

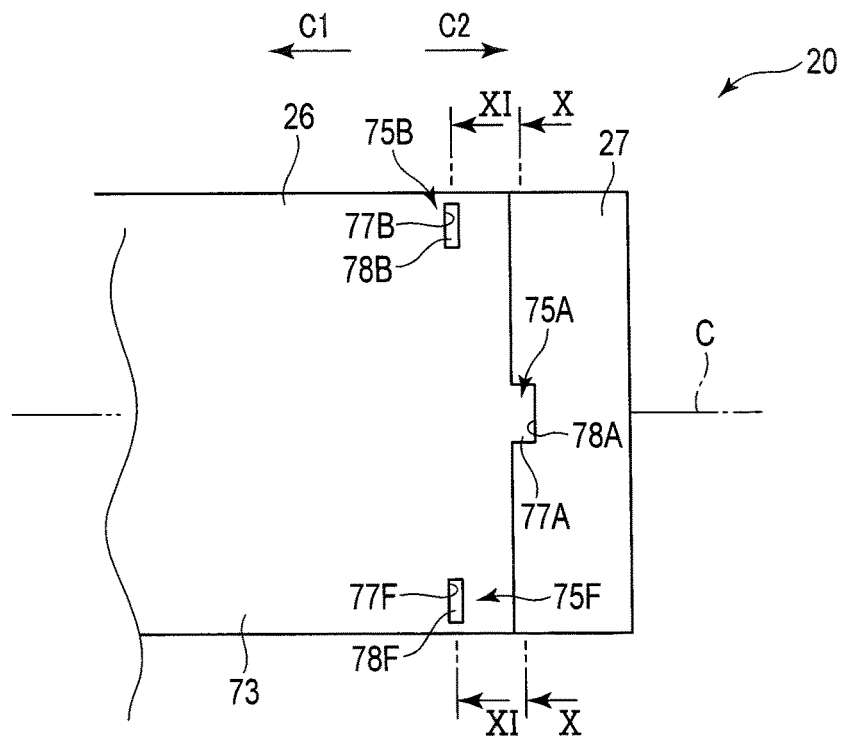
F I G. 9
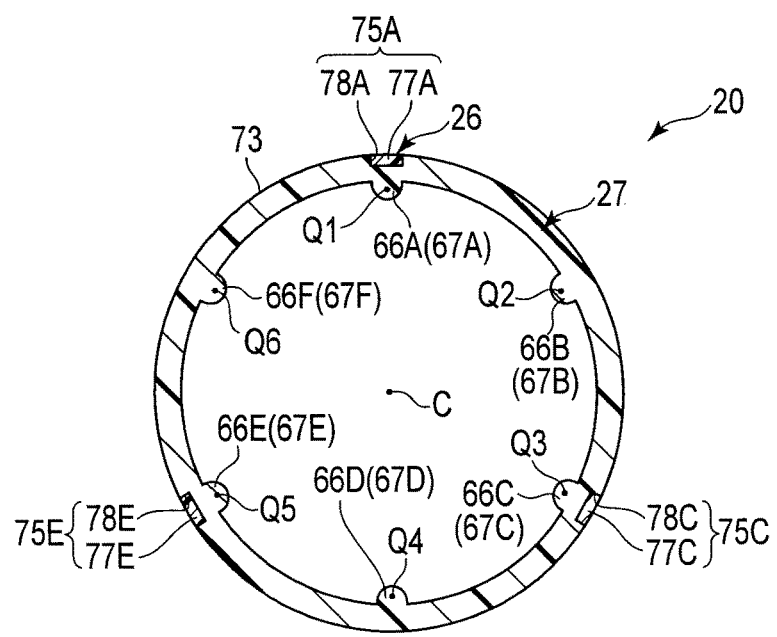
F I G. 10

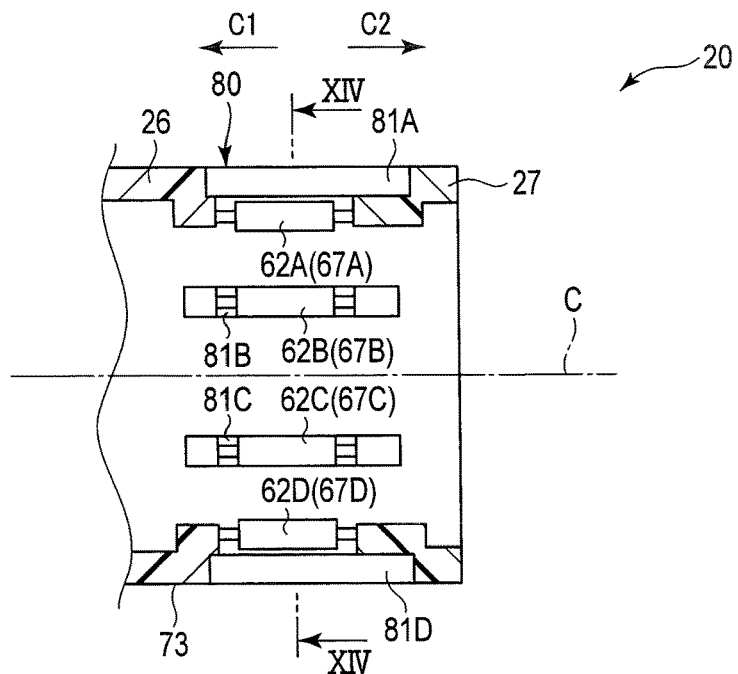
F I G. 13
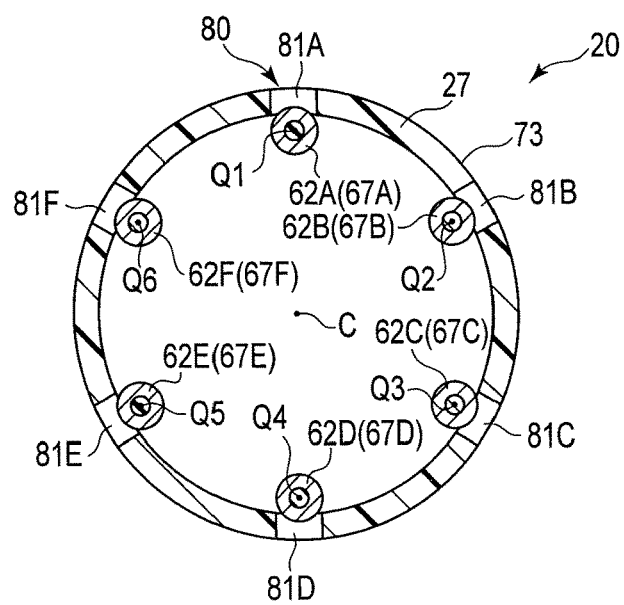
F I G. 14

INSERTION INSTRUMENT AND INSERTION DEVICE

CROSS-REFERENCE TO RELATED APPLICATIONS

This is a Continuation application of PCT Application No. PCT/JP2016/059723, filed Mar. 25, 2016 and based upon and claiming the benefit of priority from prior Japanese Patent Application No. 2015-114889, filed Jun. 5, 2015, the entire contents of which are incorporated herein by reference.

BACKGROUND OF THE INVENTION

1. Field of the Invention

The present invention relates to an insertion device in which a rotor provided in an insertion section rotates, whereby press force is applied from a first projection of the rotor to a second projection of an assistance tool, and the assistance tool attached to the insertion section rotates together with the rotor. The present invention also relates to the assistance tool provided in the insertion device.

2. Description of the Related Art

International Publication No. 2013/038720 discloses a spiral unit (assistance tool) which is attached to an insertion section of an endoscope (insertion instrument). The spiral unit which is removably attached to the insertion section in a state to cover the insertion section from the outer peripheral side, and which includes a spiral fin spirally extends around a longitudinal axis. A rotor is provided in the insertion section, and the rotor is attached to a base portion of the insertion section in a state to be rotatable around the longitudinal axis. First projections (first rollers) are provided in the rotor, and second projections (second rollers) are provided in the spiral unit. The rotor rotates around the longitudinal axis by the transmission of driving force thereto, whereby press force is applied from each of the first projections to the corresponding second projection in a rotation direction of the rotor. Due to the application of the press force from each of the first projections to the corresponding second projection, the driving force is transmitted to the spiral unit, and the spiral unit rotates relative to the base portion around the longitudinal axis. Due to the rotation of the spiral unit around the longitudinal axis in a state where the spiral fin is pressed to an inner peripheral side, propulsive force toward a distal side or a proximal side is applied to the insertion section and the spiral unit.

BRIEF SUMMARY OF THE INVENTION

According to one aspect of the invention, an assistance tool attached to an insertion section in a state to cover a rotor from an outer peripheral side in an insertion device, the insertion device including the insertion section extending from a proximal side to a distal side along a longitudinal axis, the insertion section being provided with the rotor which is configured to rotate around the longitudinal axis by the transmission of driving force thereto, the rotor including a first projection protruding toward the outer peripheral side on an outer peripheral surface of the rotor, the assistance tool including: a second projection which protrudes toward an inner peripheral side on an inner peripheral surface of the assistance tool, and which is configured to rotate the assistance tool around the longitudinal axis together with the rotor when press force is applied from the first projection to the second projection by the rotation of the rotor; and a recognition realizing unit which is configured to permit an angular position of the second projection around the longitudinal axis to be recognized from an outside of the assistance tool.

According to one another aspect of the invention, an insertion device including: an insertion section extending from a proximal side to a distal side along a longitudinal axis; a rotor which is provided in the insertion section, and which is configured to rotate around the longitudinal axis by the transmission of driving force thereto; a first projection protruding toward an outer peripheral side on an outer peripheral surface of the rotor; an assistance tool attached to the insertion section in a state to cover the rotor from the outer peripheral side; a second projection which protrudes toward an inner peripheral side on an inner peripheral surface of the assistance tool, and which is configured to rotate the assistance tool around the longitudinal axis together with the rotor when press force is applied from the first projection to the second projection by the rotation of the rotor; and a recognition realizing unit which is configured to permit an angular position of the second projection around the longitudinal axis to be recognized from an outside of the assistance tool.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 9 is a plan view seen from the outside of the spiral unit, schematically showing the proximal portion of the spiral unit according to a certain modification of the first embodiment;

FIG. 10 is a sectional view taken along the line X-X in FIG. 9;

FIG. 13 is a sectional view schematically showing the proximal portion of the spiral unit through a section parallel to a longitudinal axis, according to the second embodiment;

FIG. 14 is a sectional view taken along the line XIV-XIV in FIG. 13;

DETAILED DESCRIPTION OF THE INVENTION

First Embodiment

Figure 1:
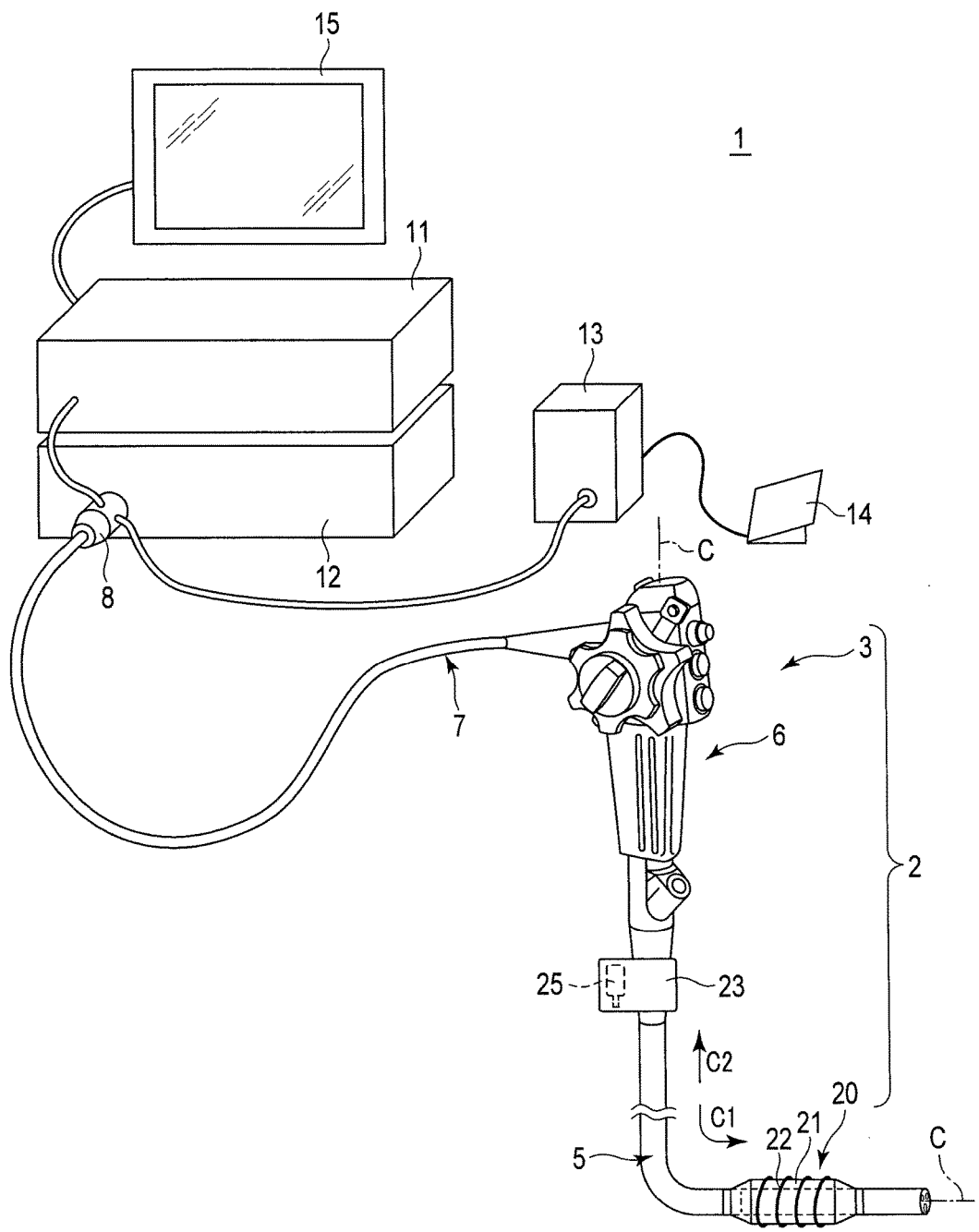
FIG. 1 is a perspective view schematically showing an endoscope system in which an endoscope device is used according to a first embodiment.

A first embodiment of the present invention is described with reference to FIG. 1 to FIG. 8. FIG. 1 is a diagram showing an endoscope system 1 in which an endoscope device 2 that is an insertion device is used. As shown in FIG. 1, the endoscope device 2 includes an endoscope 3 which is an insertion instrument, and a spiral unit 20 which is an assistance tool. The endoscope 3 includes an insertion section 5, and the insertion section 5 has a longitudinal axis C. Here, a direction along the longitudinal axis C is a longitudinal direction. One side in the longitudinal direction is a distal side (an arrow C1 side in FIG. 1), and the side opposite to the distal side is a proximal side (an arrow C2 side in FIG. 1). The insertion section 5 extends from the proximal side to the distal side along the longitudinal axis C, and an operation section 6 is provided on the proximal side with respect to the insertion section 5 in the endoscope 3. The endoscope 3 includes a universal cord 7 having one end connected to the operation section 6. A scope connector 8 is provided at the other end of the universal cord 7.

As peripheral devices, the endoscope system 1 includes an image processing device 11 such as an image processor, a light source device 12 such as a lamp, a driving control device 13, an operation input device 14 such as a foot switch, and a display device 15 such as a monitor. The universal cord 7 is removably connected to the light source device 12 via the scope connector 8. In the endoscope 3, an imaging cable (not shown) and a light guide (not shown) extend through the inside of the insertion section 5, the inside of the operation section 6, and the inside of the universal cord 7. An imaging element (not shown) such as a CCD is provided in the distal portion of the insertion section 5. The imaging element images a subject through an observation window (not shown) provided on the outer surface of the distal portion of the insertion section 5. An imaging signal is then transmitted to the image processing device 11 via the imaging cable, and image processing is performed in the image processing device 11. Thus, an image of the subject is generated in the image processing device 11, and the generated image of the subject is displayed on the display device 15. Light emitted from the light source device 12 is guided through the light guide. The guided light is then applied to the subject from an illumination window (not shown) provided on the outer surface of the distal portion of the insertion section 5.

In the endoscope device 2, the spiral unit (assistance tool) 20 is removably attached to the insertion section 5 in a state where the insertion section 5 is inserted through the spiral unit 20. In a state where the spiral unit 20 is attached to the insertion section 5, the spiral unit 20 is substantially coaxial with the insertion section 5. The spiral unit 20 includes a cylindrical tube main body 21 extending along the longitudinal axis C, and a spiral fin 22 protruding toward the outer peripheral side on the outer peripheral surface of the tube main body 21. The spiral fin 22 spirally extends around the longitudinal axis C. The spiral unit (assistance tool) 20 is rotatable around the longitudinal axis C.

In the endoscope 3, a motor casing 23 is attached to the operation section 6. An electric motor 25 which is a driving member is provided inside the motor casing 23. One end of an electric wiring line (not shown) is connected to the electric motor 25. The electric wiring line is connected to the driving control device 13 through the inside of the operation section 6 and the inside of the universal cord 7. The driving control device 13 controls the supply state of driving electric power to the electric motor 25 on the basis of an operation input in the operation input device 14, and controls the driving state of the electric motor 25. A processor or an integrated circuit including a central processing unit (CPU) or an application specific integrated circuit (ASIC) or the like, and a storage medium such as a memory are provided in the driving control device 13. The electric motor 25 is driven by the supply of the driving electric power to the electric motor 25, and driving force to rotate (revolve) the spiral unit 20 around the longitudinal axis C is generated.

Figure 2:
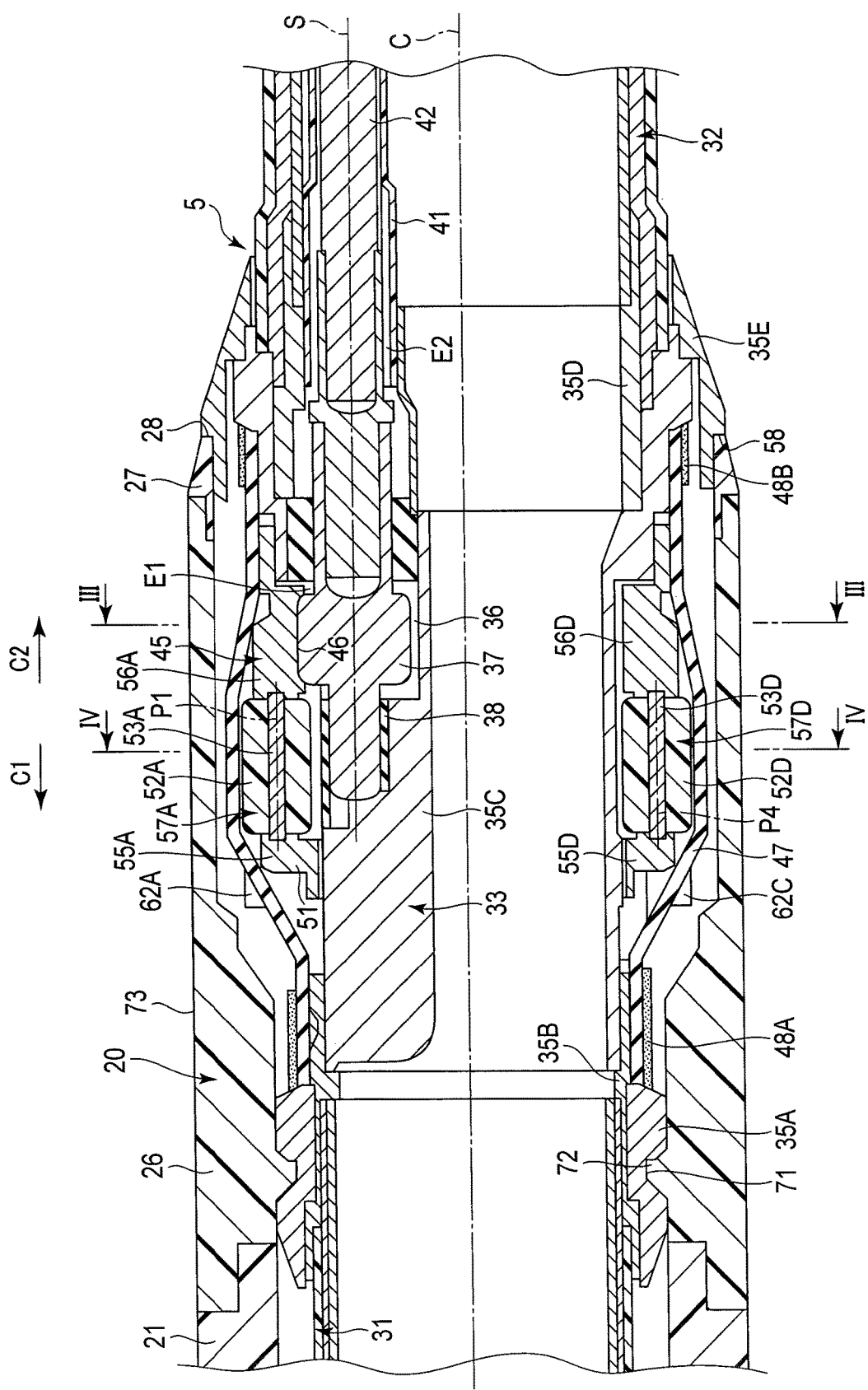
FIG. 2 is a sectional view schematically showing the configurations of the insertion section and the spiral unit in an attachment part in which a spiral unit is attached to an insertion section and in the vicinity of the attachment part, in a state where the spiral unit is attached to the insertion section, according to the first embodiment.

FIG. 2 is a diagram showing the configurations of the insertion section 5 and the spiral unit 20 in an attachment part in which the spiral unit 20 is attached to the insertion section 5 and in the vicinity of this part. FIG. 2 shows a state where the spiral unit 20 is attached to the insertion section 5. In FIG. 2, the imaging cable, the light guide, and others are omitted. As shown in FIG. 2, the insertion section 5 includes a distal side flexible tube section 31, and a proximal side flexible tube section 32 provided on the proximal side with respect to the distal side flexible tube section 31. The proximal end of the proximal side flexible tube section 32 is connected to the operation section 6. A base portion 33 made of a rigid material is provided between the distal side flexible tube section 31 and the proximal side flexible tube section 32.

That is, the distal side flexible tube section 31 is coupled to the proximal side flexible tube section 32 via the base portion 33. In a state where the spiral unit 20 is attached to the insertion section 5, the outer peripheral side of the base portion 33 is covered with the proximal portion of the spiral unit 20, and the spiral unit 20 extends toward the distal side from a part located on the outer peripheral side of the base portion 33. Although the base portion 33 is formed by the coupling of five coupling members 35A to 35E in the present embodiment, the number of members that form the base portion 33 is not limited to this, and, for example, the base portion 33 may be integrally formed from one member.

Figure 3:
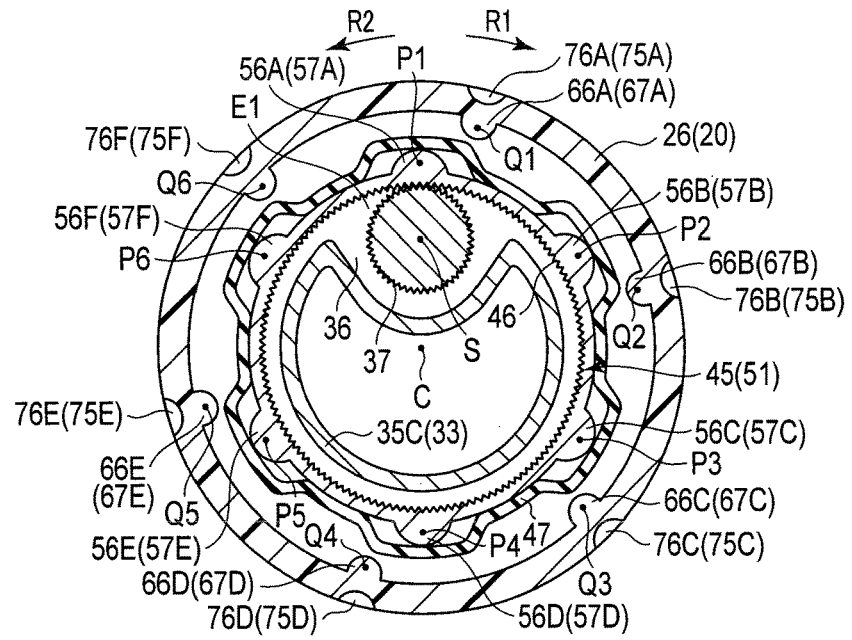
FIG. 3 is a sectional view taken along the line III-III in FIG. 2.
Figure 4:
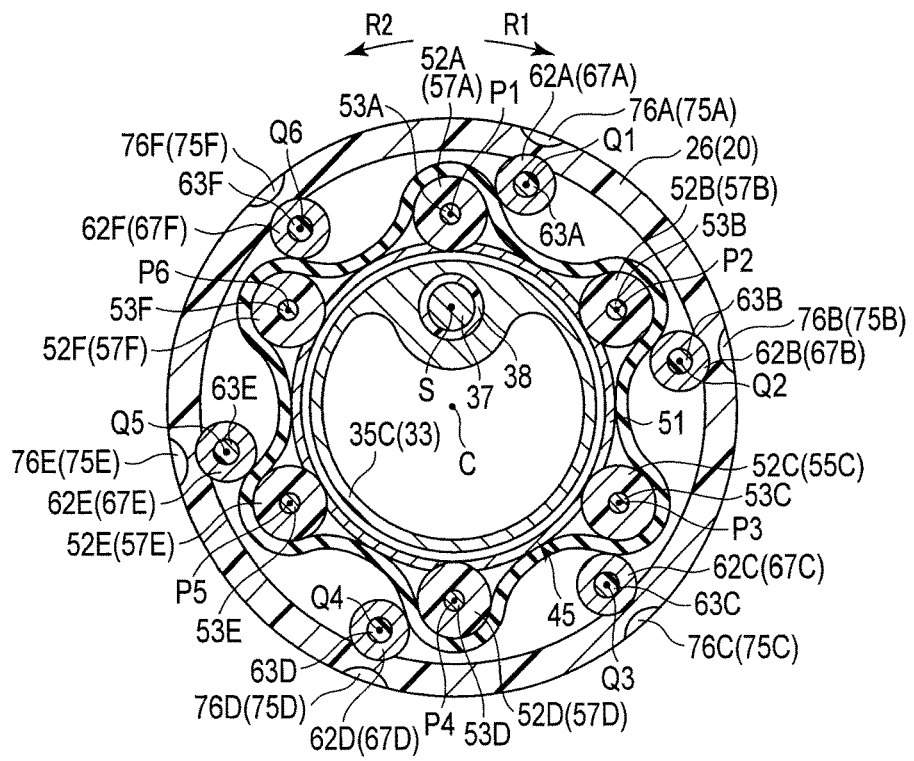
FIG. 4 is a sectional view taken along the line IV-IV in FIG. 2.

FIG. 3 is a sectional view taken along the line III-III in FIG. 2. FIG. 4 is a sectional view taken along the line IV-IV in FIG. 2. Therefore, FIG. 3 and FIG. 4 show the sections perpendicular to the longitudinal axis C. As shown in FIG. 2 to FIG. 4, a cavity 36 is formed by the base portion 33 in the insertion section 5. The cavity 36 is open toward the outer peripheral side at a first opening position E1, and open at a second opening position E2 toward the space where the imaging cable, the light guide (both are not shown), and others extend. In the cavity 36, a driving gear 37 is attached to the base portion 33 (coupling member 35C) via a support member 38. Inside the proximal side flexible tube section 32, a channel tube 41 extends from the proximal side to the distal side. The distal end of the channel tube 41 is connected to the base portion 33 (coupling member 35D) at the second opening position E2. Inside the channel tube 41, a driving shaft 42 extends along a shaft axis S which is substantially parallel to the longitudinal axis C. The distal end of the driving shaft 42 is inserted into the cavity 36 from the second opening position E2, and connected to the driving gear 37. The proximal end of the driving shaft 42 is coupled to the electric motor 25 via a gear (not shown) or the like. When the electric motor 25 is driven, driving force is transmitted to the driving shaft 42, and the driving shaft 42 rotates around the shaft axis S. As a result, the driving force is transmitted to the driving gear 37, and the driving gear 37 rotates.

The insertion section 5 includes a cylindrical rotor 45 which is attached to the base portion 33 in a state to cover the base portion 33 (coupling member 35C) from the outer peripheral side. The rotor 45 is rotatable relative to the base portion 33 around the longitudinal axis C. An inner peripheral gear portion 46 is provided on the inner peripheral surface of the rotor 45. The inner peripheral gear portion 46 extends whole circumference around the longitudinal axis C. The driving gear 37 is in mesh with the inner peripheral gear portion 46 at the first opening position E1 of the cavity 36. Thus, the driving force is transmitted to the rotor 45 by the rotation of the driving gear 37, and the rotor 45 rotates around the longitudinal axis C.

Figure 5:
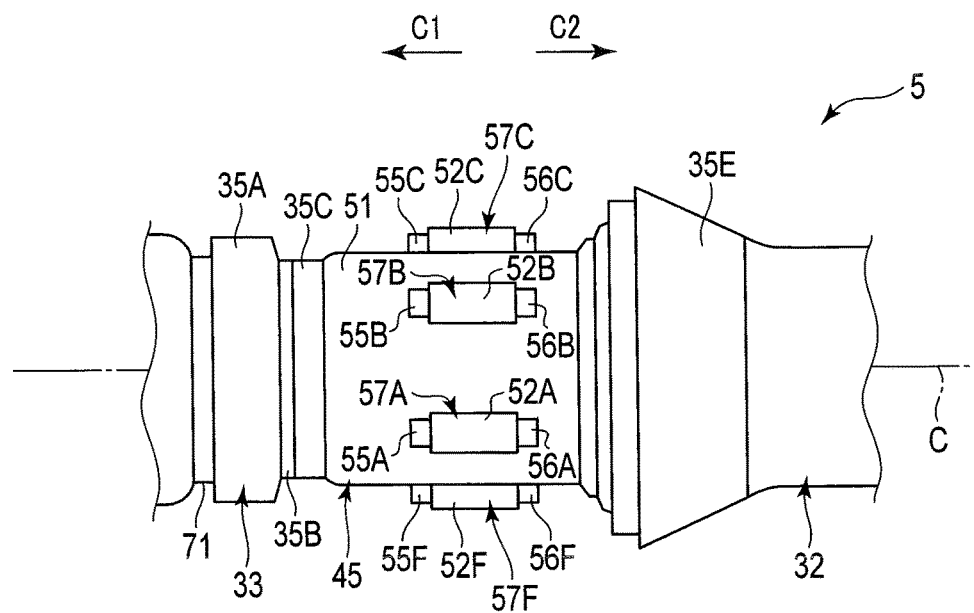
FIG. 5 is a plan view seen from the outside of the insertion section, schematically showing the configuration of the insertion section in the attachment part in which the spiral unit is attached to the insertion section and in the vicinity of the attachment part, according to the first embodiment, wherein a cover tube is omitted.

FIG. 5 shows the configuration of the insertion section 5 in an attachment part in which the spiral unit 20 is attached to the insertion section 5 and in the vicinity of this part. In FIG. 5, a cover tube 47 which will be described later is omitted. As shown in FIG. 2 to FIG. 5, the rotor 45 includes a tubular rotating member 51, and (in the present embodiment, six) first rollers (inner rollers) 52A to 52F are attached to the tubular rotating member 51. Each of the first rollers 52A to 52F is attached to the tubular rotating member 51 via the corresponding first roller shaft (corresponding one of 53A to 53F). The tubular rotating member 51 includes first distal side shaft receivers 55A to 55F and first proximal side shaft receivers 56A to 56F. To each of the first distal side shaft receivers 55A to 55F, the distal end of the corresponding first roller shaft (corresponding one of 53A to 53F) is connected. To each of the first proximal side shaft receivers 56A to 56F, the proximal end of the corresponding first roller shaft (corresponding one of 53A to 53F) is connected.

In the rotor 45, each of the first rollers 52A to 52F cooperates with the corresponding first distal side shaft receiver (corresponding one of 55A to 55F) and the corresponding first proximal side shaft receiver (corresponding one of 56A to 56F) to form a first projection (corresponding one of 57A to 57F). Each of the first projections (inner projections) 57A to 57F protrudes toward the outer peripheral side on the outer peripheral surface of the rotor 45, and has a first projection axis (corresponding one of P1 to P6) as a central axis. The first projection axes P1 to P6 are substantially parallel to the longitudinal axis C, and in the present embodiment, each of the first roller shafts (inner first roller shafts) 53A to 53F extends along the corresponding first projection axis (corresponding one of P1 to P6). Each of the first rollers 52A to 52F is turnable (rotatable) relative to the tubular rotating member 51 around the corresponding first projection axis (corresponding one of P1 to P6). That is, each of the first projection axes P1 to P6 is a turning axis of the corresponding first roller (corresponding one of 52A to 52F). The first projections 57A to 57F (the first rollers 52A to 52F) are provided apart from one another around the longitudinal axis C, and in the present embodiment, the first projections 57A to 57F are arranged at substantially equal intervals around the longitudinal axis C.

In the insertion section 5, the cylindrical cover tube 47 which covers the rotor 45 from the outer peripheral side is provided. The cover tube 47 is made of, for example, rubber, and is flexible. A part of the outer surface of the insertion section 5 is formed by the cover tube 47. The distal end of the cover tube 47 is located on the distal side with respect to the distal end of the rotor 45, and fixed to the base portion 33 (coupling member 35B) by an adhesive member 48A. The proximal end of the cover tube 47 is located on the proximal side with respect to the proximal end of the rotor 45, and fixed to the base portion 33 (coupling member 35C) by an adhesive member 48B. At the distal and proximal ends of the cover tube 47, liquid tightness is maintained between the base portion 33 and the cover tube 47. This prevents the inflow of liquid from the outside of the insertion section 5 to the inner peripheral side of the cover tube 47, and prevents the inflow of liquid from the outside of the insertion section 5 to the part in which the rotor 45 is disposed and to the cavity 36 where the driving gear 37 is disposed. The rotor 45 is rotatable relative to the cover tube 47 around the longitudinal axis C.

The spiral unit (assistance tool) 20 is removably attached to the insertion section 5 in a state where the proximal portion of the spiral unit 20 covers the cover tube 47 from the outer peripheral side. Therefore, the cover tube 47 is disposed between the rotor 45 and the spiral unit 20 in a state where the cover tube 47 covers the rotor 45 from the outer peripheral side. That is, in a state where the spiral unit (assistance tool) 20 is attached to the insertion section 5, the spiral unit 20 is located on the outer peripheral side with respect to the rotor 45 and the cover tube 47, and the rotor 45 is located on the inner peripheral side with respect to the cover tube 47. The cover tube 47 protrudes toward the outer peripheral side at angular positions (places) where the first projections 57A to 57F are located around the longitudinal axis C. Thus, even if the rotor 45 is covered from the outer peripheral side by the cover tube 47, the angular positions of the first projections 57A to 57F around the longitudinal axis C are visually recognizable (recognizable) from the outside of the insertion section 5.

The spiral unit 20 includes a cylindrical first connector (first coupling member) 26 coupled to the proximal side of the tube main body 21, and a cylindrical second connector (second coupling member) 27 coupled to the proximal side of the first connector 26. In a state where the spiral unit 20 is attached to the insertion section 5, the first connector 26 and the second connector 27 are located on the outer peripheral side of the base portion 33. A proximal end face 28 of the spiral unit 20 is formed by the second connector 27. In the coupling member 35E of the base portion 33, a receiving surface 58 on which the proximal end face 28 of the spiral unit 20 can abut is formed. The receiving surface 58 is located on the proximal side with respect to the proximal end of the rotor 45. The proximal end face 28 of the spiral unit 20 abuts on the receiving surface 58, so that the movement of the spiral unit 20 toward the proximal side from the receiving surface 58 is prevented.

An engagement groove 71 recessed toward the inner peripheral side is provided on the outer peripheral surface of the coupling member 35A of the base portion 33. The engagement groove 71 is located on the distal side with respect to the distal end of the rotor 45. The engagement groove 71 is formed whole circumference around the longitudinal axis C. An engagement claw 72 which protrudes toward the inner peripheral side is provided in the inner peripheral surface of the first connector 26 of the spiral unit 20. When the spiral unit 20 is attached to the insertion section 5, the engagement claw 72 engages with the engagement groove 71. This regulates the movement of the spiral unit 20 relative to the insertion section 5 in the longitudinal direction along the longitudinal axis C. Because the movement of the spiral unit 20 against the insertion section 5 in the longitudinal direction is regulated, detachment of the spiral unit 20 from the insertion section 5 is prevented in a state where the spiral unit 20 is rotating around the longitudinal axis C by the transmission of driving force thereto.

Figure 6:
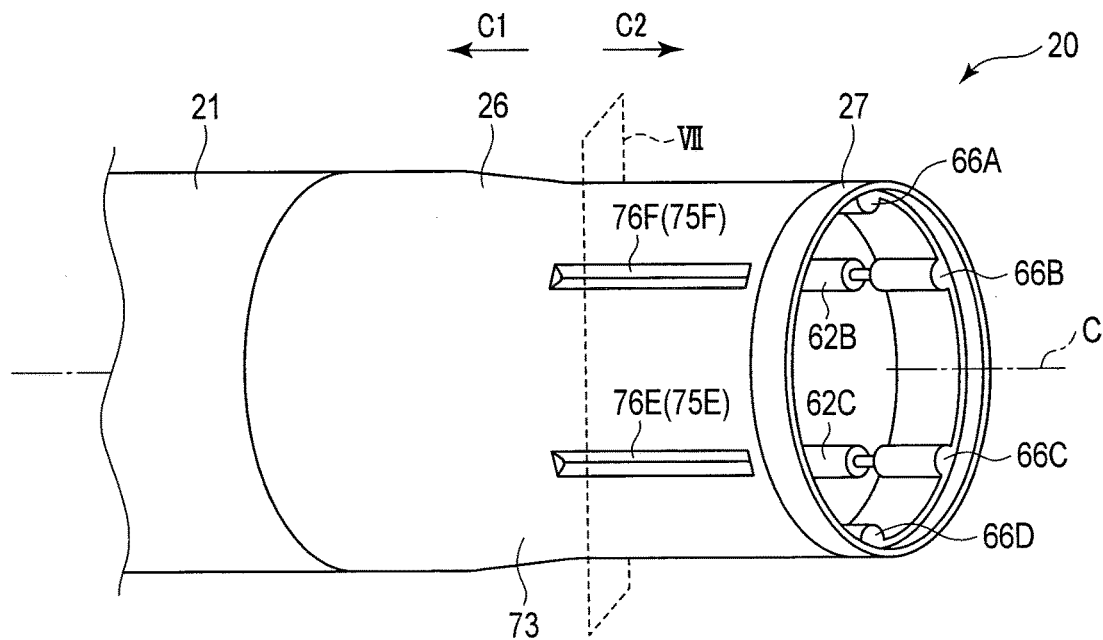
FIG. 6 is a perspective view schematically showing the configuration of a proximal portion of the spiral unit according to the first embodiment.
Figure 7:
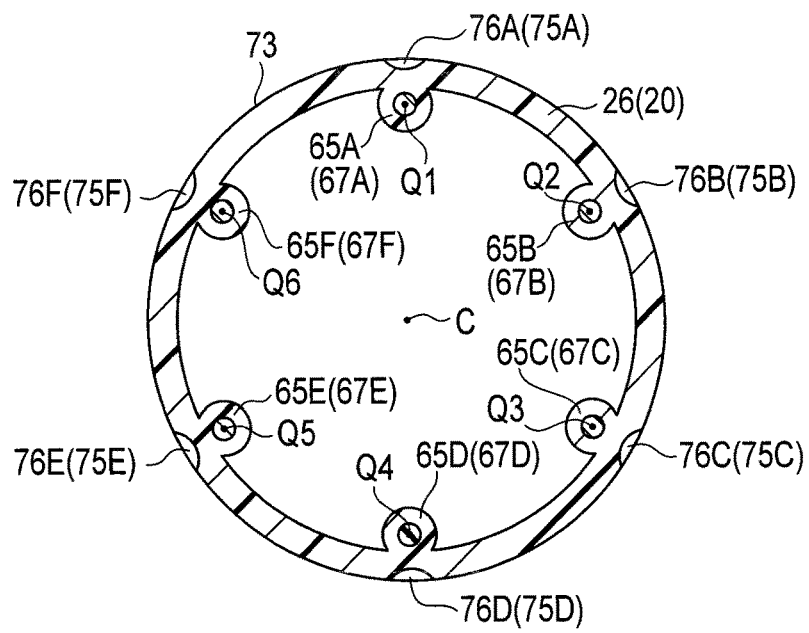
FIG. 7 is a sectional view showing a section VII in FIG. 6.

FIG. 6 is a view showing the configuration of the proximal portion of the spiral unit 20. FIG. 7 is a view showing a section VII in FIG. 6. As shown in FIG. 2 to FIG. 4, FIG. 6, and FIG. 7, (in the present embodiment, six) second rollers (outer rollers) 62A to 62F attached to the first connector 26 and the second connector 27 are provided in the proximal portion of the spiral unit 20. The second rollers 62A to 62F are located on the proximal side with respect to the engagement claw 72. Each of the second rollers 62A to 62F is attached to the first connector 26 and the second connector 27 via a corresponding second roller shaft (corresponding one of 63A to 63F). Second distal side shaft receivers 65A to 65F are formed in the first connector 26, and second proximal side shaft receivers 66A to 66F are formed in the second connector 27. The distal end of the corresponding second roller shaft (corresponding one of 63A to 63F) is connected to each of the second distal side shaft receivers 65A to 65F, and the proximal end of the corresponding second roller shaft (corresponding one of 63A to 63F) is connected to each of the second proximal side shaft receivers 66A to 66F.

In the spiral unit (assistance tool) 20, each of the second rollers 62A to 62F cooperates with the corresponding second distal side shaft receiver (corresponding one of 65A to 65F) and the corresponding second proximal side shaft receiver (corresponding one of 66A to 66F) to form a corresponding second projection (corresponding one of 67A to 67F). Each of the second projections (outer projections) 67A to 67F protrudes toward the inner peripheral side on the inner peripheral surface of the spiral unit 20, and has a second projection axis (corresponding one of Q1 to Q6) as a central axis. The second projection axes Q1 to Q6 are substantially parallel to the longitudinal axis C, and in the present embodiment, each of the second roller shafts (outer roller shafts) 63A to 63F extends along the corresponding second projection axis (corresponding one of Q1 to Q6). Each of the second rollers 62A to 62F is turnable (rotatable) relative to the first connector 26 and the second connector 27 (the tube main body 21) around the corresponding second projection axis (corresponding one of Q1 to Q6). That is, each of the second projection axes Q1 to Q6 is a turning axis of the corresponding second roller (corresponding one of 62A to 62F).

The second projections 67A to 67F (the second rollers 62A to 62F) are provided apart from one another around the longitudinal axis C, and in the present embodiment, the second projections 67A to 67F are arranged at substantially equal intervals around the longitudinal axis C. In a state where the spiral unit 20 is attached to the insertion section 5, each of the second projections 67A to 67F is disposed between corresponding two of the first projections 57A to 57F around the longitudinal axis C, and for example, the second projection 67A is disposed between the first projection 57A and the first projection 57B around the longitudinal axis C.

When the driving force is transmitted to the rotor 45 as described above and the rotor 45 rotates toward one side (an arrow R1 side in each of FIGS. 3 and 4) around the longitudinal axis C, each of the first projections 57A to 57F applies press force to the corresponding second projection (corresponding one of 67A to 67F) in a rotation direction of the rotor 45 (in this case, clockwise around the longitudinal axis C in FIG. 4) via the cover tube 47. For example, the first projection 57A applies press force to the second projection 67A via the cover tube 47. Consequently, the second projections 67A to 67F receive the driving force from the rotor 45, and the spiral unit 20 rotates relative to the base portion 33 together with the rotor 45 toward one side around the longitudinal axis C.

When the rotor 45 rotates toward the other side (an arrow R2 side in each of FIGS. 3 and 4) around the longitudinal axis C, each of the first projections 57A to 57F applies press force to the corresponding second projection (corresponding one of 67A to 67F) different from that in the case where the rotor 45 rotates toward one side around the longitudinal axis C, in a rotation direction of the rotor 45 (in this case, counterclockwise around the longitudinal axis C in FIG. 4) via the cover tube 47. For example, the first projection 57A applies press force to the second projection 67F via the cover tube 47. Consequently, the second projections 67A to 67F receive the driving force from the rotor 45, and the spiral unit 20 rotates relative to the base portion 33 together with the rotor 45 toward the other side around the longitudinal axis C.

When the spiral unit 20 rotates around the longitudinal axis C in a state where the spiral fin 22 is pressed to the inner peripheral side, propulsive force toward the distal side or the proximal side (one side in the longitudinal direction) is applied to the insertion section 5 and the spiral unit 20. In a state where the rotor 45 and the spiral unit 20 rotate together, the cover tube 47 does not rotate. However, in this instance, in each of the first projections 57A to 57F, the corresponding first roller (corresponding one of 52A to 52F) turns (rotates), so that friction between the first projections 57A to 57F (the first rollers 52A to 52F) and the cover tube 47 is lower. Similarly, in each of the second projections 67A to 67F, the corresponding second roller (corresponding one of 62A to 62F) turns (rotates), so that friction between the second projections 67A to 67F (the second rollers 62A to 62F) and the cover tube 47 is lower.

As shown in FIG. 6 and FIG. 7, the spiral unit 20 includes an exposure surface 73 which is exposed to the outside of the spiral unit 20. (In the present embodiment, six) grooves 76A to 76F recessed toward the inner peripheral side on the exposure surface 73 are provided in the first connector (first coupling member) 26. Each of the grooves 76A to 76F extends along the longitudinal axis C. An index (corresponding one of 75A to 75F) is formed by each of the grooves 76A to 76F, and each of the indexes 75A to 75F is visually recognizable from the outside of the spiral unit 20 on the exposure surface 73.

Each of the indexes 75A to 75F is located at the same angular position as the corresponding second projection (corresponding one of 67A to 67F) around the longitudinal axis C. For example, the index 75A is located at the same angular position as the second projection 67A (the second roller 62A) around the longitudinal axis C. Thus, each of the indexes 75A to 75F indicates the angular position of the corresponding second projection (corresponding one of 67A to 67F) around the longitudinal axis C. Therefore, by the visual recognition of each of the indexes 75A to 75F from the outside of the spiral unit 20, the angular position of the corresponding second projection (corresponding one of 67A to 67F) around the longitudinal axis C is recognized. That is, a recognition realizing unit which is configured to permit the angular position of the corresponding second projection (corresponding one of 67A to 67F) around the longitudinal axis C to be recognized from the outside of the spiral unit 20 is constituted by each of the indexes 75A to 75F.

Next, functions and advantageous effects of the endoscope device 2 which is the insertion device according to the present embodiment are described. When a lumen is observed by use of the endoscope device 2, the spiral unit (assistance tool) 20 is attached to the insertion section 5, and the insertion section 5 and the spiral unit 20 are inserted into the lumen. On the basis of an operation input in the operation input device 14, the electric motor 25 is driven, and driving force is transmitted to the spiral unit 20 as described above. As a result, the spiral unit 20 rotates around the longitudinal axis (revolution axis) C. When the spiral unit 20 rotates in a state where the spiral fin 22 is pressed to the inner peripheral side by a luminal wall, propulsive force toward the distal side or the proximal side (one side in a direction parallel to the longitudinal axis C) is applied to the insertion section 5 and the spiral unit 20. Mobility of the insertion section 5 in the lumen is improved by the propulsive force.

Here, when the spiral unit 20 is attached to the insertion section 5, the insertion section 5 is inserted into the spiral unit 20 from the distal end, and the spiral unit 20 is moved toward the proximal side relative to the insertion section 5 along the longitudinal axis C. The spiral unit 20 is then moved to the proximal side up to a position where the proximal end face 28 of the spiral unit 20 abuts on the receiving surface 58 of the base portion 33 and where the engagement claw 72 of the spiral unit 20 engages with the engagement groove 71 of the base portion 33, and the spiral unit 20 is thereby attached to the insertion section 5.

Figure 8:
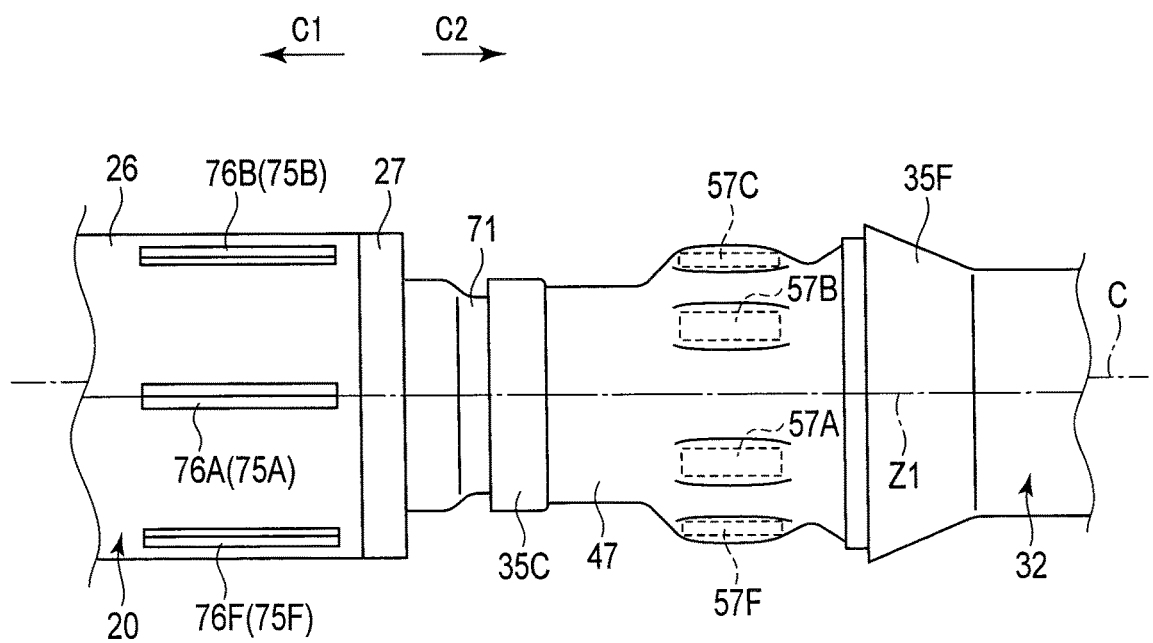
FIG. 8 is a plan view seen from the outside of the spiral unit, schematically showing a state where the spiral unit is moved toward a proximal side relative to the insertion section in the attachment of the spiral unit to the insertion section, according to the first embodiment.

FIG. 8 is a view showing a state where the spiral unit 20 is moved toward the proximal side relative to the insertion section 5 in the attachment of the spiral unit 20 to the insertion section 5. As shown in FIG. 8, when the spiral unit 20 is moved to the proximal side against the insertion section 5, the angular position of each of the indexes 75A to 75F (the grooves 76A to 76F) is adjusted to a state where each of the indexes 75A to 75F (the grooves 76A to 76F) is located apart from any one of the first projections 57A to 57F (the first rollers 52A to 52F) around the longitudinal axis C. For example, the angular position of the index 75A is adjusted to a state where the index 75A is located between the first projection 57A and the first projection 57B around the longitudinal axis C, and the index 75A is located apart from any one of the first projections 57A to 57F around the longitudinal axis C. Therefore, a virtual straight line Z1 extending to the proximal side from the index 75A along the longitudinal axis C passes between the first projection 57A and the first projection 57B around the longitudinal axis C, and passes the position which is apart from any one of the first projections 57A to 57F around the longitudinal axis C.

At the angular positions (places) where the first projections 57A to 57F are located around the longitudinal axis C, the cover tube 47 protrudes toward the outer peripheral side, so that the angular positions of the first projections 57A to 57F around the longitudinal axis C can be visually recognized from the outside of the insertion section 5. Because the indexes 75A to 75F are exposed to the outside of the spiral unit 20 on the exposure surface 73, the angular positions of the indexes 75A to 75F around the longitudinal axis C can be visually recognized from the outside of the spiral unit 20. Thus, when the spiral unit 20 is moved toward the proximal side relative to the insertion section 5, each of the indexes 75A to 75F can be easily adjusted to the angular position which is apart from any one of the first projections 57A to 57F around the longitudinal axis C, without visual recognition of the spiral unit 20 from the inner peripheral side (inner side).

In the present embodiment, each of the indexes 75A to 75F is located at the same angular position as the corresponding second projection (corresponding one of 67A to 67F) around the longitudinal axis C, and by the visual recognition of each of the indexes 75A to 75F from the outside of the spiral unit 20, the angular position of the corresponding second projection (corresponding one of 67A to 67F) around the longitudinal axis C is recognized. Thus, when each of the indexes 75A to 75F is located at the angular position which is apart from any one of the first projections 57A to 57F around the longitudinal axis C, each of the second projections 67A to 67F (the second rollers 62A to 62F) of the spiral unit 20 is adjusted to the angular position which is apart from any one of the first projections 57A to 57F around the longitudinal axis C.

Each of the second projections 67A to 67F is located at the angular position which is apart from any one of the first projections 57A to 57F around the longitudinal axis C, whereby when the spiral unit 20 is moved in the proximal side relative to the insertion section 5, interference of each of the second projections 67A to 67F with the first projections 57A to 57F from the distal side is prevented. By the adjustment of the angular position of each of the indexes 75A to 75F around the longitudinal axis C, the angular position of the corresponding second projection (corresponding one of 67A to 67F) around the longitudinal axis C is adjusted, so that when the spiral unit 20 is moved toward the proximal side relative to the insertion section 5, it is not necessary to visually recognize the angular positions of the second projections 67A to 67F around the longitudinal axis C from the inner peripheral side (inner side) of the spiral unit 20. Therefore, the spiral unit (assistance tool) 20 can be easily attached to the insertion section 5.

When the spiral unit 20 is moved toward the proximal side relative to the insertion section 5, each of the second projections 67A to 67F does not interfere with any one of the first projections 57A to 57F from the distal side. This prevents the cover tube 47 from being caught between the distal end of a certain first projection (any one of 57A to 57F) and the proximal end of a certain second projection (any one of 67A to 67F). That is, when the spiral unit 20 is moved in the proximal side relative to the insertion section 5, the cover tube 47 is prevented from being caught between a certain first projection (any one of 57A to 57F) and a certain second projection (any one of 67A to 67F) in the longitudinal direction. This prevents an excessive load on the cover tube 47 when the spiral unit 20 is moved toward the proximal side relative to the insertion section 5.

Modifications of First Embodiment

Figure 11:
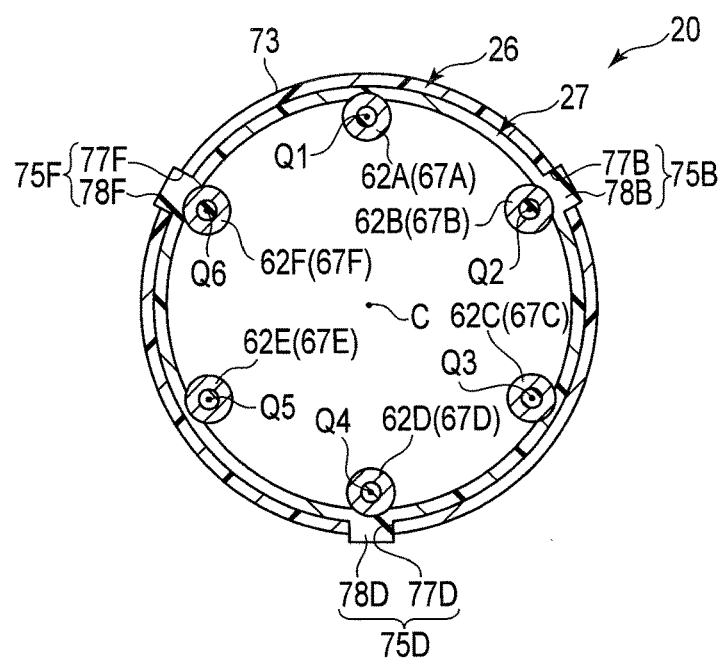
FIG. 11 is a sectional view taken along the line XI-XI in FIG. 9.

A certain modification of the first embodiment is described with reference to FIG. 9 to FIG. 11. FIG. 9 shows the proximal portion of the spiral unit 20 according to a certain modification in a plane seen from the outside. FIG. 10 is a sectional view taken along the line X-X in FIG. 9. FIG. 11 is a sectional view taken along the line XI-XI in FIG. 9.

As shown in FIG. 9 to FIG. 11, (in the present modification, three) engagement pieces (first engagement portions) 77A, 77C, and 77E protruding toward the proximal side are provided in the first connector (first coupling member) 26 in the present modification. (In the present modification, three) engagement grooves (second engagement portions) 78A, 78C, and 78E recessed toward the proximal side are provided in the second connector (second coupling member) 27. Moreover, (in the present modification, three) engagement holes (first engagement portions) 77B, 77D, and 77F pierced from the outer peripheral surface to the inner peripheral surface of the first connector 26 are provided in the first connector 26. In the second connector 27, (in the present modification, three) engagement claws (second engagement portions) 78B, 78D, and 78F protruding to the outer peripheral side are provided on the outer peripheral surface of the second connector 27. Each of the engagement grooves 78A, 78C, and 78E engages with the corresponding engagement piece (corresponding one of 77A, 77C, and 77E), and each of the engagement claws 78B, 78D, and 78F engages with the corresponding engagement hole (corresponding one of 77B, 77D, and 77F), whereby the second connector 27 is coupled to the first connector 26.

Each of the engagement grooves 78A, 78C, and 78E engages with the corresponding engagement piece (corresponding one of 77A, 77C, and 77E) in a state where each of the engagement grooves 78A, 78C, and 78E is exposed to the outside of the spiral unit 20 on the exposure surface 73. The index (corresponding one of 75A, 75C, and 75E) is formed by an engagement part of each of the engagement grooves 78A, 78C, and 78E and the corresponding engagement piece (corresponding one of 77A, 77C, and 77E), and each of the indexes 75A, 75C, and 75E can be visually recognized from the outside of the spiral unit 20 on the exposure surface 73. Each of the engagement claws 78B, 78D, and 78F engages with the corresponding engagement hole (corresponding one of 77B, 77D, and 77F) in a state where each of the engagement claws 78B, 78D, and 78F is exposed to the outside of the spiral unit 20 on the exposure surface 73. The index (corresponding one of 75B, 75D, and 75F) is formed by an engagement part of each of the engagement claws 78B, 78D, and 78F and the corresponding engagement hole (corresponding one of 77B, 77D, and 77F), and each of the indexes 75B, 75D, and 75F can be visually recognized from the outside of the spiral unit 20 on the exposure surface 73.

In the present modification as well, each of the indexes 75A to 75F is located at the same angular position as the corresponding second projection (corresponding one of 67A to 67F) around the longitudinal axis C. Thus, each of the indexes 75A to 75F indicates the angular position of the corresponding second projection (corresponding one of 67A to 67F) around the longitudinal axis C. Therefore, by the visual recognition of each of the indexes 75A to 75F from the outside of the spiral unit 20, the angular position of the corresponding second projection (corresponding one of 67A to 67F) around the longitudinal axis C is recognized.

In another certain modification, each of the indexes 75A to 75F may be formed by a pattern printed on the exposure surface 73 of the spiral unit 20. In this case, a figure such as an arrow, or a line different in color from other parts is printed as the pattern on the exposure surface 73. In the present modification as well, each of the indexes 75A to 75F is located, for example, at the same angular position as the corresponding second projection (corresponding one of 67A to 67F) around the longitudinal axis C, and each of the indexes 75A to 75F indicates the angular position of the corresponding second projection (corresponding one of 67A to 67F) around the longitudinal axis C.

Although the same number of indexes 75A to 75F as the second projections 67A to 67F are provided in the embodiment and others described above, this is not a limitation. For example, in a certain modification, the six second projections (67A to 67F) are provided, whereas only three indexes (75A, 75C, and 75E) may be provided. In this case as well, the indexes (75A, 75C, and 75E) are visually recognizable from the outside of the spiral unit 20, and each of the indexes (75A, 75C, and 75E) indicates the angular position of the corresponding second projection (corresponding one of 67A, 67C, and 67E) around the longitudinal axis C.

Furthermore, in a certain modification, only one index (75A) may be provided. In this case as well, the index (75A) is visually recognizable on the exposure surface 73 from the outside of the spiral unit 20. The index (75A) is located at the same angular position as the second projection (67A) around the longitudinal axis C, and indicates the angular position of the corresponding second projection (67A) around the longitudinal axis C. In the present modification, in the attachment of the spiral unit 20 to the insertion section 5, the index (75A) is located at the angular position which is apart from any one of the first projections (57A to 57F) around the longitudinal axis C when the spiral unit 20 is moved toward the proximal side relative to the insertion section 5. As a result, the second projection (67A) is adjusted to the angular position which is apart from any one of the first projections 57A to 57F around the longitudinal axis C. In the configuration in which the first projections (57A to 57F) are arranged at substantially equal intervals around the longitudinal axis C and in which the second projections (67A to 67F) are arranged at substantially equal intervals around the longitudinal axis C, when one second projection (67A) is located at the angular position which is apart from any one of the first projections (57A to 57F) around the longitudinal axis C, each of the other second projections (67B to 67F) is also located at the angular position which is apart from any one of the first projections (57A to 57F) around the longitudinal axis C.

In the first embodiment and its modifications, the indexes (75A to 75F; 75A, 75C, and 75E; 75A) which are visually recognizable from the outside are provided in the spiral unit (20). Each of the indexes (75A to 75F; 75A, 75C, and 75E; 75A) indicates the angular position of the corresponding second projection (corresponding one of 67A to 67F; corresponding one of 67A, 67C, and 67E; 67A) around the longitudinal axis C.

Second Embodiment

Next, a second embodiment of the present invention is described with reference to FIG. 12 to FIG. 14. The second embodiment is the following modification of the configuration according to the first embodiment. The same parts as those in the first embodiment are denoted by the same reference signs and are not described.

Figure 12:
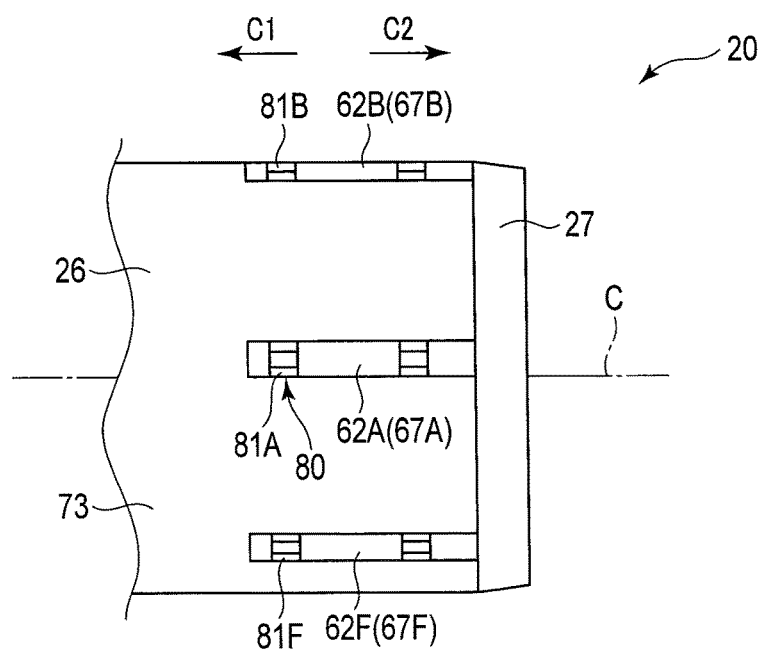
FIG. 12 is a plan view seen from the outside of the spiral unit, schematically showing the proximal portion of the spiral unit according to a second embodiment.

FIG. 12 shows the proximal portion of the spiral unit 20 in a plane seen from the outside. FIG. 13 shows a section of the proximal portion of the spiral unit 20 parallel to the longitudinal axis C. FIG. 14 is a sectional view taken along the line XIV-XIV in FIG. 13. As shown in FIG. 12 to FIG.

14, in the present modification, holes 81A to 81F which pierce the first connector 26 from the outer peripheral surface (the exposure surface 73) to the inner peripheral surface are formed in the first connector 26. In the present embodiment, each of the holes 81A to 81F extends along the longitudinal axis C, and located at the same angular position as the corresponding second projection (corresponding one of 67A to 67F) around the longitudinal axis C. Through each of the holes 81A to 81F, the corresponding second projection (corresponding one of 67A to 67F) can be visually recognized from the outside of the spiral unit 20. Thus, the angular position of each of the second projections 67A to 67F around the longitudinal axis C is visually recognizable (recognizable) from the outside of the spiral unit 20.

That is, in the present embodiment, a visualizing portion 80 which permits the second projections 67A to 67F to be visually recognized from the outside of the spiral unit (assistance tool) 20 is provided in the spiral unit 20, and the holes 81A to 81F are formed in the first connector 26 by the visualizing portion 80. Moreover, a recognition realizing unit which is configured to permit the angular positions of the second projections 67A to 67F around the longitudinal axis C to be recognized from the outside of the spiral unit 20 is constituted by the visualizing portion 80.

In the attachment of the spiral unit 20 to the insertion section 5, the spiral unit 20 is moved toward the proximal side relative to the insertion section 5 while the angular position of each of the second projections 67A to 67F around the longitudinal axis C is visually recognized through the holes 81A to 81F. Each of the second projections 67A to 67F is then adjusted to the angular position which is apart from any one of the first projections 57A to 57F around the longitudinal axis C. Thus, in the present embodiment as well, when the spiral unit 20 is moved toward the proximal side relative to the insertion section 5, each of the second projections 67A to 67F can be easily adjusted to the angular position which is apart from any one of the first projections 57A to 57F around the longitudinal axis C, without visual recognition of the spiral unit 20 from the inner peripheral side (inner side). Therefore, advantageous effects similar to those in the first embodiment are provided in the present embodiment as well.

In the present embodiment, each of the holes 81A to 81F is located at the same angular position as the corresponding second projection (corresponding one of 67A to 67F) around the longitudinal axis C. Thus, each of the holes 81A to 81F also serves as an index indicating the angular position of the corresponding second projection (corresponding one of 67A to 67F) around the longitudinal axis C.

Modifications of Second Embodiment

In a certain modification of the second embodiment, each of the holes 81A to 81F may be located at the angular position which is apart from any one of the second projections 67A to 67F around the longitudinal axis C. In this case as well, at least one second projection (at least one of 67A to 67F) can be visually recognized from the outside of the spiral unit 20 through each of the holes 81A to 81F.

The number of the holes (81A to 81F) is not limited to six. For example, in a certain modification, only three holes (81A, 81C, and 81E) may be provided, or in another certain modification, only one hole (81A) may be provided. When the holes (81A to 81F; 81A, 81C, and 81E; 81A) are formed in the spiral unit 20 by the visualizing portion 80, at least one second projection (at least one of 67A to 67F) has only to be visually recognizable from the outside of the spiral unit 20 through the holes (81A to 81F; 81A, 81C, and 81E; 81A). Consequently, in the configuration in which the second projections (67B to 67F) are arranged at substantially equal intervals around the longitudinal axis C, the angular positions of all the second projections (67A to 67F) around the longitudinal axis C can be recognized from the outside of the spiral unit 20.

Figure 15:
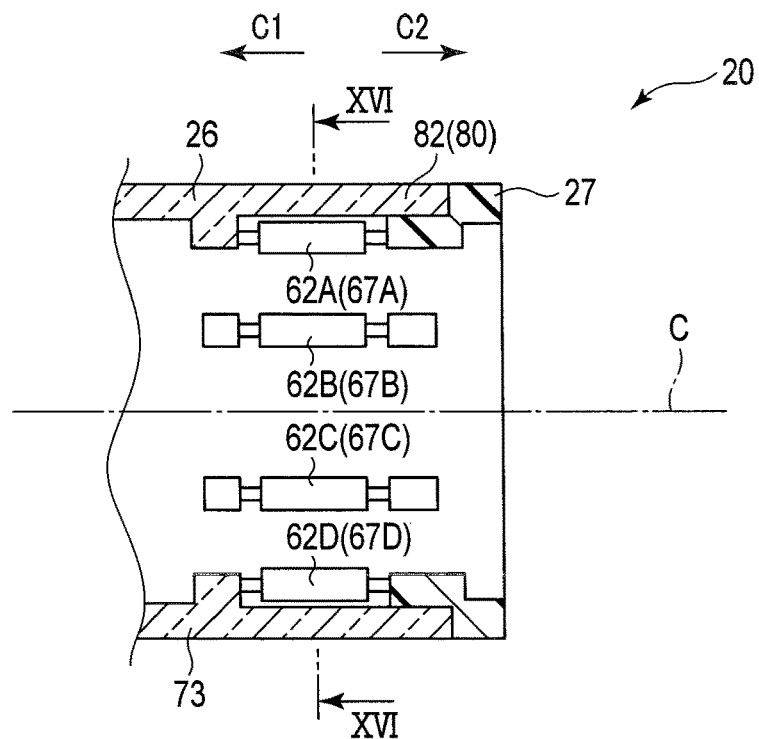
FIG. 15 is a sectional view schematically showing the proximal portion of the spiral unit through the section parallel to the longitudinal axis, according to a certain modification of the second embodiment.
Figure 16:
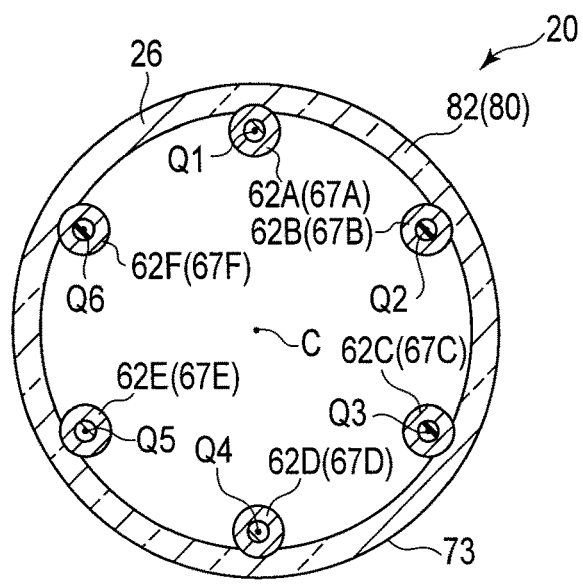
FIG. 16 is a sectional view taken along the line XVI-XVI in FIG. 15.

Another certain modification of the second embodiment is described with reference to FIG. 15 and FIG. 16. FIG. 15 shows the proximal portion of the spiral unit 20 according to the modification through the section parallel to the longitudinal axis C. FIG. 16 is a sectional view taken along the line XVI-XVI in FIG. 15.

As shown in FIG. 15 and FIG. 16, in the present modification, the first connector 26 is made of, for example, a skeleton material. Thus, the whole first connector 26 is a high transmittance part 82 which is higher in light transmittance than other parts (the second connector 27, the tube main body 21, and others) of the spiral unit 20. In the present modification, the visualizing portion 80 which is configured to permit the second projections 67A to 67F to be visually recognized from the outside of the spiral unit (assistance tool) 20 is formed by the high transmittance part 82. Therefore, in the present modification as well, the angular positions of the second projections 67A to 67F around the longitudinal axis C can be recognized from the outside of the spiral unit 20.

The high transmittance part 82 is preferably transparent, but does not need to be transparent if the high transmittance part 82 has a degree of light transmittance that permits the second projections 67A to 67F to be visually recognized from the outside of the spiral unit (assistance tool) 20. Moreover, the high transmittance part 82 does not need to be provided in the whole first connector 26, and has only to be provided at a position where one of the second projections 67A to 67F can be visually recognized from the outside of the spiral unit 20 through the high transmittance part 82. For example, in a certain modification, the high transmittance part 82 is not provided whole circumference around the longitudinal axis C, but is only provided within a part of the angular range around the longitudinal axis C.

In the second embodiment and its modifications, the visualizing portion (80) is provided in the spiral unit (20). At least one of the second projections (67A to 67F) can be visually recognized from the outside of the spiral unit (20) by the visualizing portion (80).

Other Modifications

Although each of the first projections 57A to 57F is provided with the corresponding turnable first roller (corresponding one of 52A to 52F) and each of the second projections 67A to 67F is provided with the corresponding turnable second roller (corresponding one of 62A to 62F) in the embodiment and others described above, this is not a limitation. For example, in a certain modification, the first projections 57A to 57F are not provided with no turnable rollers, and the first projections 57A to 57F are formed integrally with a tubular rotating member 51. The second projections 67A to 67F are not provided with turnable rollers, and the second projections 67A to 67F are formed integrally with the first connector 26.

The number of the first projections (inner projections) 57A to 57F and the number of the second projections (outer projections) 67A to 67F are not limited to those in the embodiments described above. In a certain modification, the rotor 45 may be provided with three first projections (e.g.

57A to 57C) at substantially equal intervals around the longitudinal axis C, or may be provided with only one first projection (57A). Similarly, the spiral unit 20 may be provided with three second projections (e.g. 67A to 67C) at substantially equal intervals around the longitudinal axis C, or may be provided with only one second projection (67A). The spiral unit (20) which is the assistance tool has only to rotate around the longitudinal axis C together with the rotor (45) when press force is applied from each of the first projections (57A to 57F; 57A to 57C; 57A) to the corresponding second projection (corresponding one of 67A to 67F; corresponding one of 67A to 67C; 67A) by the rotation of the rotor (45).

Although the spiral unit (20) is described by way of example as the assistance tool which is attached to the insertion section (5) in the embodiments and others described above, the assistance tool is not limited to the spiral unit (20). Although the endoscope (2) is described by way of example as the insertion instrument in the embodiments and others described above, the insertion instrument is not limited to the endoscope (2). For example, the configuration described above may be applied to an insertion surgical system in which a manipulator is used as the insertion instrument.

In a certain modification, no cover tube (47) may be provided between the rotor (45) and the assistance tool (20). In this case, each of the first projections (57A to 57F) contacts the corresponding second projection (corresponding one of 67A to 67F) by the rotation of the rotor (45) around the longitudinal axis (C). Accordingly, press force is applied from each of the first projections (57A to 57F) to the corresponding second projection (corresponding one of 67A to 67F) in the rotation direction of the rotor (45), and the spiral unit (20) rotates around the longitudinal axis (C).

In the embodiments and others described above, the insertion device (2) includes the insertion section (5) extending from the proximal side to the distal side along the longitudinal axis (C), the rotor (45) which is provided in the insertion section (5) and which is configured to rotate around the longitudinal axis (C) by the transmission of driving force thereto, and the assistance tool (20) which is attached to the insertion section (5) in a state to cover the rotor (45) from the outer peripheral side. The first projections (57A to 57F) protrude toward the outer peripheral side on the outer peripheral surface of the rotor (45), and the second projections (67A to 67F) protrude toward the inner peripheral side on the inner peripheral surface of the assistance tool (20). The assistance tool (20) is configured to rotate around the longitudinal axis (C) together with the rotor (45) when press force is applied from the first projections (57A to 57F) to the second projections (67A to 67F) by the rotation of the rotor (45). The angular positions of the second projections (67A to 67F) around the longitudinal axis (C) can be recognized from the outside of the assistance tool (20) by the recognition realizing unit (75A to 75F; 80).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An assistance tool for attachment to an insertion section so as to cover a rotor from an outer peripheral side of the insertion section, the insertion section extending from a proximal side to a distal side along a longitudinal axis, the rotor of the insertion section being configured to rotate around the longitudinal axis by the transmission of a driving force thereto, a first projection of the rotor protruding toward the outer peripheral side on an outer peripheral surface of the rotor, the assistance tool comprising:
    a second projection which protrudes toward an inner peripheral side on an inner peripheral surface of the assistance tool, and which is configured to receive a press force from the first projection of the rotor and then configured to rotate around the longitudinal axis due to the rotation of the rotor, thereby rotating the assistance tool around the longitudinal axis; and
    a recognition realizing unit which is provided on an outer peripheral surface of the assistance tool, and which is configured to permit an angular position of the second projection around the longitudinal axis to be recognized from an outside of the assistance tool.

2. The assistance tool according to claim 1, wherein the recognition realizing unit includes an index which indicates the angular position of the second projection around the longitudinal axis, and which is visually recognizable from the outside of the assistance tool.

3. The assistance tool according to claim 2, further comprising an exposure surface which is exposed to the outside of the assistance tool, wherein the index is visually recognizable from the outside of the assistance tool on the exposure surface.

4. The assistance tool according to claim 3, wherein the index includes a groove recessed toward the inner peripheral side on the exposure surface.

5. The assistance tool according to claim 3, wherein the index includes a pattern printed on the exposure surface.

6. The assistance tool according to claim 3, further comprising:
    a first coupling member; and a second coupling member which is coupled to the first coupling member,
    wherein the index includes a first engagement portion provided in the first coupling member, and a second engagement portion which is provided in the second coupling member and which is configured to couple the second coupling member to the first coupling member by engaging with the first engagement portion in a state where the second engagement portion is exposed to the outside of the assistance tool on the exposure surface.

7. The assistance tool according to claim 2, wherein the index is located at the same angular position as the second projection around the longitudinal axis.

8. The assistance tool according to claim 1, wherein the recognition realizing unit includes a visualizing portion which is configured to permit the second projection to be visually recognized from the outside of the assistance tool.

9. The assistance tool according to claim 8, wherein the visualizing portion forms a hole in the assistance tool, and is configured to permit the second projection to be visually recognized from the outside of the assistance tool through the hole.

10. The assistance tool according to claim 8, further comprising, as the visualizing portion, a high transmittance part which is higher in light transmittance than other parts of the assistance tool, and which is configured to permit the second projection to be visually recognized from the outside of the assistance tool through the high transmittance part.

11. An insertion device comprising:
    an insertion section extending from a proximal side to a distal side along a longitudinal axis;

a rotor which is provided in the insertion section, and which is configured to rotate around the longitudinal axis by the transmission of a driving force thereto;

a first projection protruding toward an outer peripheral side on an outer peripheral surface of the rotor;

an assistance tool attached to the insertion section so as to cover the rotor from the outer peripheral side;

a second projection which protrudes toward an inner peripheral side on an inner peripheral surface of the assistance tool, and which is configured to receive a press force from the first projection and then configured to rotate around the longitudinal axis due to the rotation of the rotor, thereby rotating the assistance tool around the longitudinal axis; and a recognition realizing unit which is provided on an outer peripheral surface of the assistance tool, and which is configured to permit an angular position of the second projection around the longitudinal axis to be recognized from an outside of the assistance tool.

12. The insertion device according to claim 11, wherein the insertion section includes a flexible cover tube provided between the rotor and the assistance tool so as to cover the rotor from the outer peripheral side, and the first projection is configured to apply the press force to the second projection via the cover tube.

* * * * *